United States Patent [19]

Ben-Dov

[11] Patent Number: 4,889,111

[45] Date of Patent: Dec. 26, 1989

[54] BONE GROWTH STIMULATOR

[76] Inventor: Meir Ben-Dov, 69 Woodbine Rd., New City, N.Y. 10956

[21] Appl. No.: 110,613

[22] Filed: Oct. 19, 1987

Related U.S. Application Data

[63] Continuation of Ser. No. 604,643, filed as PCT US84/00167 on Feb. 8, 1984, published as WC85/03449 on Aug. 15, 1985, abandoned.

[51] Int. Cl.$^4$ .......................... A61F 5/04; A61N 1/32
[52] U.S. Cl. ..................... 128/419 F; 606/54
[58] Field of Search ....................... 128/92 Z

[56] References Cited

U.S. PATENT DOCUMENTS

| | | | |
|---|---|---|---|
| 3,783,880 | 1/1974 | Kraus | 128/419 F |
| 3,893,462 | 7/1975 | Manning | 128/421 |
| 3,918,440 | 11/1975 | Kraus | 128/419 F |
| 4,026,304 | 5/1977 | Levy | 128/419 F |
| 4,095,602 | 6/1978 | Leveen | 128/419 R |
| 4,308,863 | 1/1982 | Fischer | 128/92 A |
| 4,365,624 | 12/1982 | Jaquet | 128/92 A |
| 4,390,023 | 6/1983 | Rise | 128/421 |
| 4,465,069 | 8/1984 | Barbier et al. | 128/303 B |

FOREIGN PATENT DOCUMENTS 818711 8/1959 United Kingdom ............ 128/303 B

OTHER PUBLICATIONS

"The Alternate Treatment of Fracture Non-Union", Published Sep. 1979, Zimmer, U.S.A.
"The Electric Connection", Published, 1981, Zimmer, Inc.

*Primary Examiner*—Francis Jaworski
*Attorney, Agent, or Firm*—Grant L. Hubbard

[57] ABSTRACT

A combined external fixation and bone growth stimulation apparatus in which current flows, in a defined cycle, from a cathode to one of two pairs of electrodes, then from one pair of electrodes to the other, and then from the cathode to the other pair of electrodes, is disclosed.

14 Claims, 2 Drawing Sheets

BONE GROWTH STIMULATOR

This is a continuation of co-pending application Ser. No. 604,643 filed as PCT US84/00167 on Feb. 8, 1984, published as WO85/03449 on Aug. 15, 1985, now abandoned.

FIELD OF THE INVENTION

This invention relates to orthopedic surgery and, more specifically, to external fixation and bone growth stimulation apparatus.

BACKGROUND OF THE INVENTION

It has been known for three decades that bone structures have bioelectric properties. It is known, for example, that bones tend to be electronegative in areas of compression and electropositive in areas of tension, and that areas of active growth and repair tend to be electronegative. Many workers have demonstrated the phenomenon of electric current stimulated osteogenesis at the cathode. Electric currents, both AC and DC, including pulsating DC, in the range of from about 10 to 100 microamperes is known to stimulate bone growth in some but not necessarily all subjects. The literature on this subject is extensive, see, e.g. Spadaro JA: Electrically Stimulated Bone Growth in Animals and Man, A review of the Literature, Clin. Orthop. 122: 325, 1977.

Implantable electric current bone growth stimulator devices have been reported, see, e.g., U.S. Pat. Nos. 3,745,995; 3,783,880; 3,890,953; 3,915,151; 3,968,790; 4,011,861; 4,052,754; 4,306,564; 4,313,438; 4,315,503; 4,333,469 and 4,414,979. Prostheses having electrically stimulated bone growth devices have also been proposed; see, e.g., U.S. Pat. Nos. 3,964,473; 4,195,367; 4,214,322 and 4,216,548. Non-invasive bone growth stimulators, see, e.g. U.S. Pat. Nos. 4,056,097; 4,066,065; 4,153,060; 4,175,565 and 4,244,373, and bone growth stimulators with specific current and voltage patterns, see, e.g., U.S. Pat. Nos. 4,105,017; 4,266,532; 4,266,533; and 4,315,503, have been described. Semi-invasive bone growth stimulators have also been disclosed, see, e.g., Zimmer, "The Alternate Treatment of Fracture Nonunion, Electrical Stimulation to Induce Osteogenesis, Zimmer USA, Warsaw, Ind. 46580, September 1979 revision, and U.S. Pat. Nos. 3,842,841 and 3,918,440.

U.S. Pat. No. 4,026,304 reviews the state of the art and early developments and is incorporated herein by reference. This patent also discusses the problem of polarization and proposes, as a solution, an implantable source of electric potential to generate a train of electric pulses.

U.S. Pat. No. 3,893,462 discloses another method of bone growth stimulation utilizing electrical signals undulating in both the positive and negative directions in an asymmetric manner reactively coupled to the bone.

The general approach in the prior art has been to provide an electric current bone growth stimulator separately from any external fixation which may be used. While efforts have been made to avoid or mitigate the problem of polarization which results when current flows in a given direction through an electrode. The present invention addresses the problems of external fixation and bone growth stimulation, including the problem of polarization.

SUMMARY OF THE INVENTION

The present invention comprises an apparatus for both fixing a bone fracture and stimulating the bone growth repair of the fracture, while eliminating or at least mitigating the effects of polarization in electric current induced osteogenesis. The present invention includes a method for accomplishing these results. The invention may be described, in its various facets as follows:

A combined external fixation device and bone growth stimulator comprising, in combination: a first pair of fixature pins for extending into a fractured bone, one pin on each side of the fracture site of the bone; a second pair of fixature pins for extending into the fractured bone, on pin on each side of the fracture site of the bone; external fixation frame means for rigidly fixing the position of said first and second pins with the distal end thereof secured to the fractured bone and the proximal end secured proximate the frame means to thereby fix the position of the fractured bone on both sides of the fracture therein and thus fixing the position of the fracture site thereof; at least one cathode each comprising a relatively rigid electrically conductive wire externally insulated along a major central portion thereof, having a biologically compatible electrically conductive distal tip for contacting the fractured bone proximate the fracture therein; means secured to the external fixation frame means for fixing the position of said cathodes with the distal tip in electrical contact with the bone proximate the fracture site therein; means electrically isolating the cathodes and pins from each other thereby preventing electrical contact with one another through the frame means; and means for applying electrical voltage to the cathodes and the pins cyclically for a a plurality of time periods during each cycle, the cathodes at all times having either no voltage or negative voltage applied thereto, the pins having either positive, negative or no voltage applied thereto, either the first pins or the second pins being positive when a negative voltage is applied to any cathode, the voltage application being cycled to cause electron flow from a cathode to the first pins in a first period, from the first pins to the second pins during a second period, from a cathode to the second pins in third period, and from the second pins to the first pins in fourth period Preferably the apparatus comprises at least two cathodes and the means for applying electrical voltage comprises means to cycle the application of voltage to cause electron flow from one cathode during the first period and from another cathode during the third period.

In a still more preferred embodiment, the apparatus includes four cathodes and the means for applying electrical voltage comprises: means for applying electrical voltage to the cathodes and the pins cyclically for a a plurality of time periods during each cycle, the cathodes at all times having either no voltage or negative voltage applied thereto, the pins having either positive, negative or no voltage applied thereto, either the first pins or the second pins being positive when a negative voltage is applied to any cathode, the voltage application being cycled to cause electron flow from a first cathode to the first pins in a first period, from the first pins to the second pins during a second period, from the second cathode to the second pins in third period, from the second pins to the first pins in fourth period, from the third cathode to the first pins in the fifth period, from the first pins to the second pins in the sixth period, from the fourth cathode to the second pins in the seventh period, and from the second pins to the first pins in the eighth period.

The invention may also be described as a combined external fixation and bone growth stimulating means comprising the combination of: first and second pairs of fixation pins; at least one cathode; frame means for electrically isolating and fixing the position of the pins and cathodes, including means for fixing the first pair of pins fixed one on each side of the fracture site of a bone, the second pair of pins one on each side of said fracture site, and the cathodes proximate said fracture site; and means for applying a voltage for a first period between a cathode and the first pins, during a second period between the first and second pins, during a third period between a cathode and the second pins, and during a fourth period between the second and first pins, the cathode being negative during the first and third periods and neutral during the second and fourth periods, the first pins being negative during the second period and positive during the fourth period.

The invention also comprehends a method of treating a bone fracture comprising the steps of: fixing the site of the bone fracture with an external fixation device, including inserting a first pair of fixation pins one on each side of said site, and inserting a second pair of fixation pins one on each side of said site; fixing at least one cathode with the distal end thereof in electrical contact with the bone adjacent the fracture site therein; and applying a voltage cyclically during odd numbered and even numbered time periods, applying said voltage during odd numbered time periods between a cathode and the pairs of pins alternately, the cathode being negative during said odd numbered cycles, applying said voltage during even numbered time periods between the pairs of pins alternately, the polarity being reversed between said pins during alternate even numbered time periods.

In a specific method of treating a bone fracture, the invention comprises the steps of: fixing the site of the bone fracture with an external fixation device, including inserting a first pair of fixation pins one on each side of said site, and inserting a second pair of fixation pins one on each side of said site; fixing a plurality of cathodes with the distal end thereof in electrical contact with the bone adjacent the fracture site therein; and applying a voltage cyclically during odd numbered and even numbered time periods, applying said voltage during odd numbered time periods between the cathodes alternately and the pairs of pins alternately, the cathode being negative during said odd numbered cycles, applying said voltage during even numbered time periods between the pairs of pins alternately, the polarity being reversed between said pins during alternate even numbered time periods.

The preferred method of treating a bone fracture according to this invention comprises the steps of: fixing the site of the bone fracture with an external fixation device, including inserting a first pair of fixation pins one on each side of said site, and inserting a second pair of fixation pins one on each side of said site; fixing at least four cathodes with the distal end thereof in electrical contact with the bone adjacent the fracture site therein; and applying a voltage cyclically during odd numbered and even numbered time periods, applying said voltage during odd numbered time periods between the cathodes alternately and the pairs of pins alternately, the cathode being negative during said odd numbered cycles, applying said voltage during even numbered time periods between the pairs of pins alternately, the polarity being reversed between said pins during alternate even numbered time periods.

In an exemplary embodiment, the method of treating a bone fracture of this invention comprises the steps of: fixing the site of the bone fracture with an external fixation device, including inserting a first pair of fixation pins one on each side of said site, and inserting a second pair of fixation pins one on each side of said site; fixing at least four cathodes with the distal end thereof in electrical contact with the bone adjacent the fracture site therein; and applying a voltage cyclically during odd numbered and even numbered time periods, the cathodes at all times having either no voltage or negative voltage applied thereto, the pins having either positive, negative or no voltage applied thereto, either the first pins or the second pins being positive when a negative voltage is applied to any cathode, the voltage application being cycled to cause electron flow from a first cathode to the first pins in a first period, from the first pins to the second pins during a second period, from the second cathode to the second pins in third period, from the second pins to the first pins in fourth period, from the third cathode to the first pins in the fifth period, from the first pins to the second pins in the sixth period, from the fourth cathode to the second pins in the seventh period, and from the second pins to the first pins in the eighth period.

DESCRIPTION OF THE PREFERRED EMBODIMENT

Figure 1:
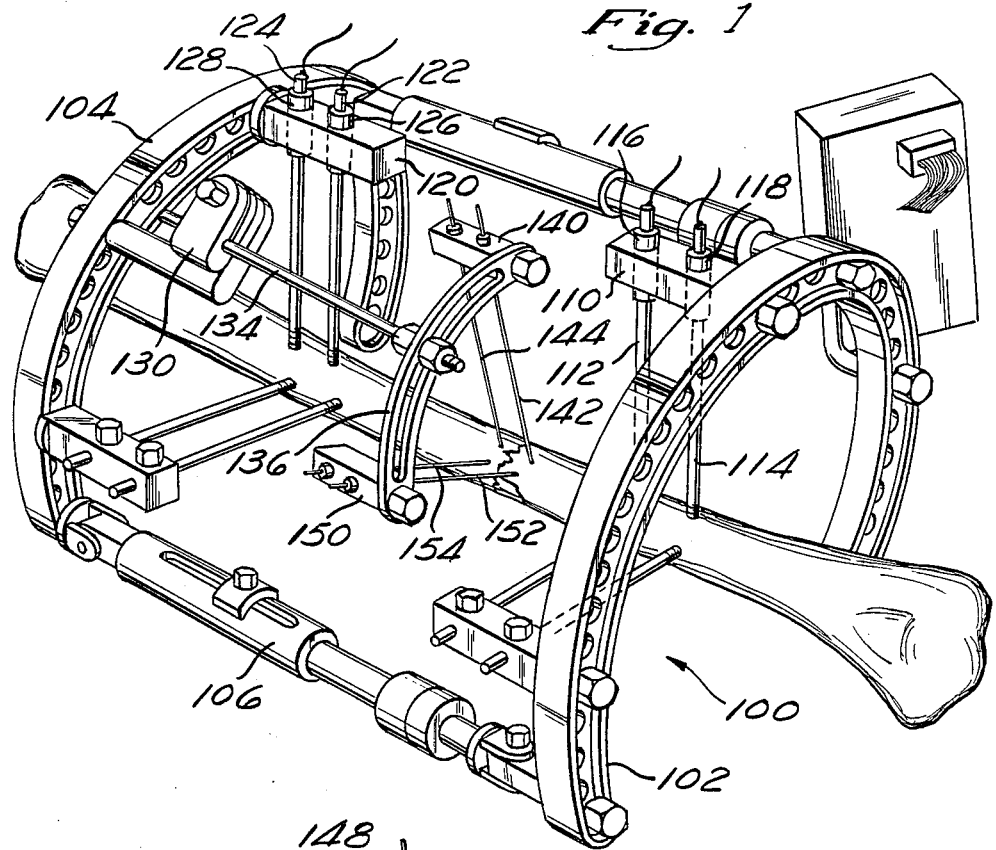
FIG. 1 is a perspective view of the apparatus of this invention, the frame being shown in simplified form.
Figure 2:
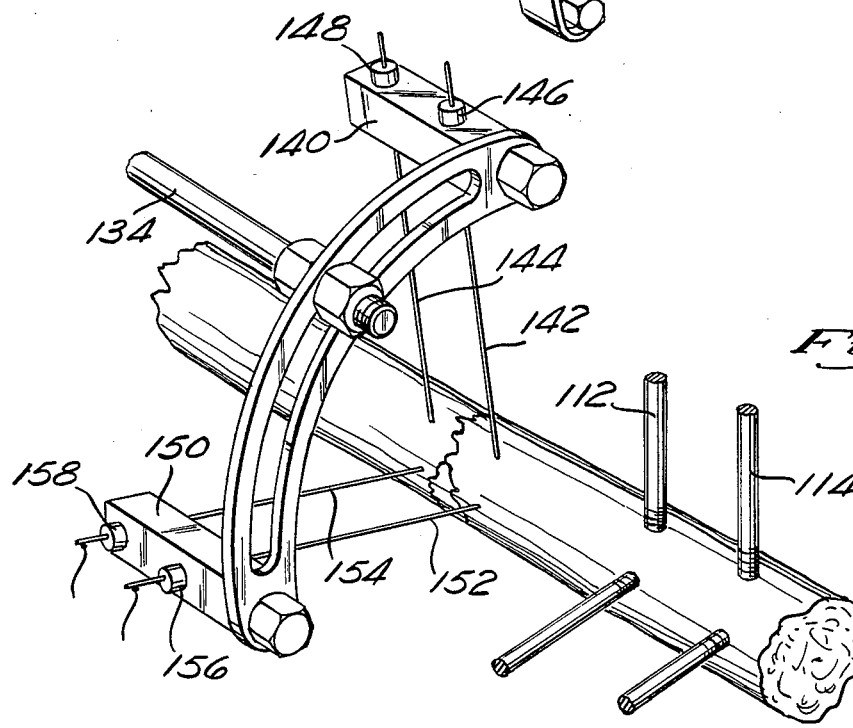
FIG. 2 is an enlarged perspective view of a portion of the apparatus of this invention.

The invention is described as applied to the Ace-Fischer (Trademark) external fixation device, which in very simplified form is shown in FIGS. 1 and 2; however, it is to be understood and emphasized that the invention includes and comprehends any external fixation device which is capable of fixing fixture pins and cathodes. The Ace-Fischer (Trademark) external fixation device is described in detail in U.S. Pat. No. 4,308,863.

The invention includes an external fixation device 100 which may be in any configuration. In the depicted embodiment, which is merely exemplary and non-limiting, the fixation device includes a pair of semicircular frame members 102 and 104 secured in spaced relation about the fractured bone by adjustable rod means one of which is depicted at 106. Pin holders 110 and 120 are secured in any convenient manner to the frame members and fix the fixture pins 112 and 114, in holder 110, and 122 and 124, in holder 120, in position. Electrically insulating means 116 and 118 in holder 110 and insulating means 126 and 128 in holder 120 electrically isolate the pins 112, 114, 122 and 124 from each other such that there is no electrical connection between them through the frame. Insulating means may be, for example, Teflon (Trademark) polytetrafluoroethylene or other insulative sleeves. The distal ends of the pins are screwed, or otherwise secured, in the usual manner to the bone. One pair of pins, 112 and 122, are secured one pin on each side of the fracture site, and the other pair of pins, 114 and 124, are secured also one pin on each side of the fracture site. The pins on each side are spaced apart sufficiently to avoid electrical shorting therebetween.

A bracket 130 secures a rod 134 to the frame means such that the rod extends approximately parallel to the axis of the bone proximate the center of the frame where it supports an arcuate mounting bracket 136. Cathode mounting blocks 140 and 150 are secured to the mounting bracket 136 in a conventional way, such as by a bolt and nut arrangement. The block 140 mounts cathodes 142 and 144 preferrable by means of electrically insulative sleeves 146 and 148. In like manner, the block 150 mounts cathodes 152 and 154 by means of sleeves 156 and 158 as will be obvious from the structure illustrated at FIGS. 1 and 2, the position of the cathodes with respect to the pins and the fractured bone by adjustment of the extension of rod 134 from bracket 130, and by movement of the arcuate mounting bracket 136 with respect to the rod 134. Thus, the lateral and axial position of the cathodes may be adjustably varied and subsequently fixed in the desired position.

As pointed out, the specific structures by which the pins and cathodes are mounted are of no consequence insofar as this invention is concerned so long as they perform the necessary function of mounting the pins in fixed relation with the distal ends of the pins secured to the bone to fix the fracture site of the bone and mounting the cathodes with the distal ends of the cathodes in electrical contact with the bone in the proximity of the fracture site. The tips of the pin may be in the fracture site, in the bone adjacent the fracture site or in the soft tissue adjacent the bone fracture site, all of which locations are referred to herein as being in electrical contact with the bone. The cathodes and pins are electrically isolated from each other, except, of course, through the bone and the source of voltage which will be described, such that a voltage can be applied between any cathode and either pair of pins and between the pairs of pins.

The means for applying a voltage is illustrated for the sole purpose of describing the manner in which the voltage is applied. It will be instantly understood that in practice solid state voltage regulators, switches, etc. will be used. Since the exact circuitry and devices for generating and applying a voltage are of no importance to the operation of the invention, so long as the voltage is applied as described, a simplified schematic representation has been selected to more clearly and simply illustrate the voltage applying means.

Figure 3:
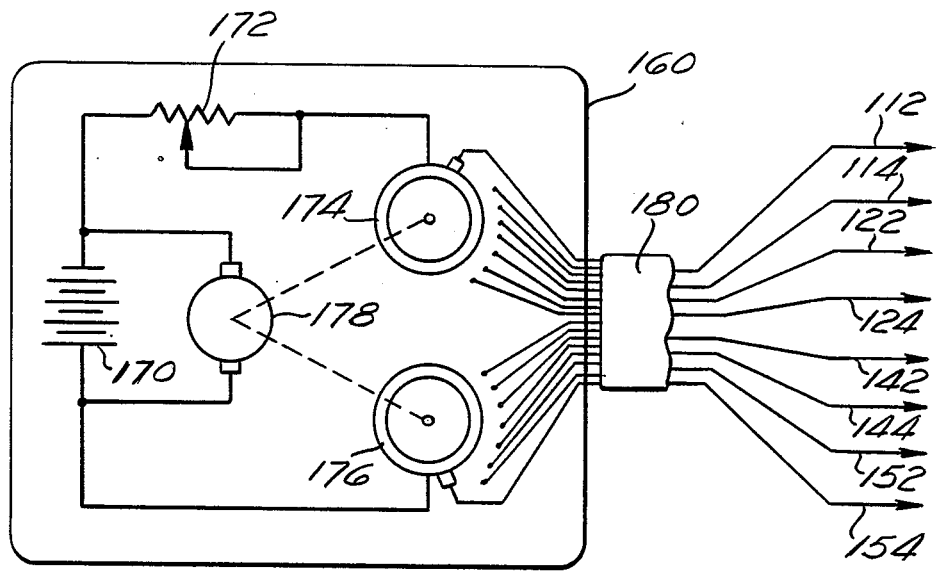
FIG. 3 is a very schematic view illustrating the principle of application of voltage to the cathodes and pins of FIGS. 1 and 2.

As shown in FIG. 3, a voltage in a particular cyclical pattern to be described is applied from the voltage applying means 170. Typically, a stable battery having long term constant voltage, indicated at 170, will be used. A current regulator depicted generally at 172 will be included. This, of course, will be a solid state device rather than the functionally schematic variable resister shown. To illustrate the cyclic manner of applying voltage, a pair of wiper switches 174 and 176 driven by motor 178 are shown simply to illustrate that the voltage will be applied sequentially to a number of electrical conductors in cable 180 and thence to the pins 112, 114, 122, and 124, and the cathodes 142, 144, 152 and 154. Again, it is emphasized that solid state switching is conveniently used and that the switching shown is functionally schematic to illustrate the principle. Since solid state circuitry of the type suitable for use in the invention is well known and conventional, and since so many circuits can suitably be used is is deemed unnecessary to describe the same in detail. Reference is made to the aforecited patents for various circuits which may used or modified for use. Reference is also made to standard electronic circuitry texts and manuals.

The operation of the voltage apply means is as follows:

In the preferred embodiment, the apparatus includes four cathodes and two sets of pins. The means for applying electrical voltage applies electrical voltage to the cathodes and the pins cyclically for a a plurality of time periods during each cycle. The cathodes at all times having either no voltage or negative voltage applied thereto. The pins having either positive, negative or no voltage applied thereto, either the first pins or the second pins being positive when a negative voltage is applied to any cathode. The conductors in cable 80 are connected to the switching mechanism such that the voltage application is cycled to cause electron flow from a first cathode to the first pins in a first period, from the first pins to the second pins during a second period, from the second cathode to the second pins in third period, from the second pins to the first pins in fourth period, from the third cathode to the first pins in the fifth period, from the first pins to the second pins in the sixth period, from the fourth cathode to the second pins in the seventh period, and from the second pins to the first pins in the eighth period.

The connection of the conductors between the switching mechanism and the cathodes and pins and the operation of the switching mechanism is fully defined by the following table.

TABLE I

| Time Period | Cathode Polarity | | | | Pin Polarity | | | |
|---|---|---|---|---|---|---|---|---|
| | 112 | 114 | 122 | 124 | 142 | 152 | 144 | 154 |
| 1 | — | 0 | 0 | 0 | + | + | 0 | 0 |
| 2 | 0 | 0 | 0 | 0 | — | — | + | + |
| 3 | 0 | — | 0 | 0 | 0 | 0 | + | + |
| 4 | 0 | 0 | 0 | 0 | + | + | — | — |
| 5 | 0 | 0 | — | 0 | + | + | 0 | 0 |
| 6 | 0 | 0 | 0 | 0 | — | — | + | + |
| 7 | 0 | 0 | 0 | — | 0 | 0 | + | + |
| 8 | 0 | .0 | 0 | 0 | + | + | — | — |

Current was controlled in the range of 5 to 20 microamperes. The full sequence of pulsing occurs at 10 Hz timed intervals. Each sequence involves eight events—four firings (negative charging of a cathode) and four discharges of the anodes (pins). Each of these eight events requires 12.5 milliseconds. Thus, the full eight events requires 100 milliseconds and the sequence repeats itself 10 times each second.

It will, of course, be understood that the specific order of voltage application is not critical and can be altered. What is important is that the electron flow be controlled such that it is always from the cathode to one or the other of the sets of pins, when the cathodes are active, and that there be period flow between the pins opposite the direction of flow when the cathode current flows to the pins. The intensity of the current does not differ from that taught in the prior art and may typically range from about 10 microamps to 100 microamps, normally being from 10 to 20 microamps. These ranges are, of course, typical and not critical.

DISCUSSION

Animal studies of the invention were conducted at the Cleveland Research Institute using a canine model. Torsional strength values were almost double for stimulated tibias as compared with a control series. The histological and microradiographic analysis demonstrated earlier evidence of cellular activity (1-2 weeks post operatively) in the stimulated groups. The 6 weeks post operative analysis showed a more dense and more mature material tibial deposit in the stimulated tibial fractures. Significantly, the incidence of pin loosening was only one-fourth as frequent in the stimulated series as in the control series. Additionally the degree of loosening was 3.5 times greater in the control series as in the stimulated series. The level of trace elements in the model was slightly higher in the stimulated series than in the control, but the difference was marginal and the levels for both groups were well within an acceptable range. It was concluded from this series that the invention was both safe and effective in promoting fracture healing in the canine model. Clinical trials are being planned and it is predicted from the animal tests that the invention will be both safe and effective in promoting human bone growth.

It will be understood that considerable variation can be made within the principle of the invention without departing therefrom, especially as regards the structure of the fixation device, the manner of producing the electric voltage for current flow, and the specific order of cycling the voltage to the cathodes and pins.

INDUSTRIAL APPLICATION

This invention will find industrial application in veterinary medicine and in orthopedic surgery.

What is claimed is:

1. A bone growth stimulator comprising, in combination:
    (a) a first pair of fixature pins for extending into a fractured bone, one pin on each side of the fracture site of the bone;
    (b) a second pair of fixature pins for extending into the fractured bone, one pin on each side of the fracture site of the bone;
    (c) means for fixing the position of said first pair and second pair of pins with the distal end thereof secured to the fractured bone to fix the position of the fractured bone or both sides of the fracture therein, and thus fixing the position of the fracture site thereof;
    (d) at least one cathode comprising an electrically conductive wire externally insulated along a major central portion thereof, having a biologically compatible electrically conductive distal tip for contacting the fractured bone proximate the fracture therein;
    (e) means for fixing the position of said at least one cathode with the distal tip in electrical contact with the bone proximate the fracture site therein;
    (f) means electrically isolating the at least one cathode and pins from each other; and
    (g) means for applying electrical voltage to the at least one cathode and the pins cyclically for a plurality of time periods during each cycle, each cathode at all times having either no voltage or negative voltage applied thereto, the pins having either positive, negative or no voltage applied thereto, either the first pins or the second pins being positive when a negative voltage is applied to any cathode, the voltage application being cycled to cause electron flow from a cathode to the first pins in a first period, from the first pins to the second pins during a second period, from a cathode to the second pins in third period, and from the second pins to the first pins in fourth period.

2. The apparatus of claim 1 comprising at least one additional cathode and wherein the means for applying electrical voltage comprises means to cycle the application of voltage to cause electron flow from one cathode during the first period and from another cathode during the third period.

3. The apparatus of claim 1 comprising three additional cathodes and wherein the means for applying electrical voltage comprises:
    means for applying electrical voltage to the cathodes and the pins cyclically for a plurality of time periods during each cycle, the cathodes at all times having either no voltage or negative voltage applied thereto, the pins having either positive, negative or no voltage applied thereto, either the first pair of pins or the second pair of pins being positive when a negative voltage is applied to any cathode, the voltage application being cycled to cause electron flow from a first cathode to the first pins in a first period, from the first pins to the second pins during a second period, from the second cathode to the second pins in third period, from the second pins to the first pins in fourth period, from the third cathode to the first pins in the fifth period, from the first pins to the second pins in the sixth period, from the fourth cathode to the second pins in the seventh period, and from the second pins to the first pins in the eighth period.

4. The bone growth stimulator of claim 1 further comprising means for adjusting the lateral position of each cathode with respect to the fractured bone.

5. The bone growth stimulator of claim 1 further comprising means for adjusting the axial position of each cathodes about the fractured bone.

6. A combined external fixation and bone growth stimulating means comprising the combination of:
    (a) first and second pairs of fixation pins;
    (b) at least one cathode;
    (c) frame means for electrically isolating and fixing the position of the pins and at least one cathode, including means for fixing the first pair of pins one on each side of the fracture site, and the at least one cathode proximate said fracture site, said frame means comprising means for adjusting the position of said at least one cathode with respect to the position of said pins and said bone; and
    (d) means for applying a voltage for a first period between a cathode and the first pairs pins, during a second period between the first and second pins pairs, during a third period between a cathode and the second pair of pins, and during a fourth period between the second and first pairs of pins, the cathode being negative during the first and third period and neutral during the second and fourth periods, the first pair of pins being negative during the second period and positive during the fourth period.

7. A bone growth stimulating means comprising the combination of:
    (a) first and second pairs of fixation pins;
    (b) first and second cathodes;
    (c) means for electrically isolating and fixing the position of the pins and cathodes, including means for fixing the first pair of pins one on each side of the fracture site of a bone, the second pair of pins one on each side of said fracture site, and the cathodes proximate said fracture site; and (d) means for adjusting the position of said cathodes with respect to the position of said pairs of pins and said bone; and (e) means for applying a voltage for a first period between the first cathode and the first pair of pins, during a second period between the first and second pairs of pins, during a third period between the second cathode and the second pins, and during a fourth period between the second and first pairs of pins, the first cathode being negative during the first and third periods and neutral during the second and fourth periods, the first pair of pins being negative during the second period and positive during the fourth period, the second cathode being neutral during the first and third periods and negative during the second and fourth periods.

8. A combined external fixation and bone growth stimulating means comprising the combination of:
   (a) first and second pairs of fixation pins;
   (b) a plurality of cathodes;
   (c) frame means for electrically isolating and fixing the position of the pins and cathodes, including means for fixing the first pair of pins one on each side of the fracture site of a bone, the second pair of pins one on each side of said fracture site, and the cathodes proximate said fracture site; and
   (d) said frame means further including means for adjusting the position of said cathodes with respect to the position of said pairs of pins and said bone; and
   (e) means for applying a voltage cyclically during time periods, said voltage applied during odd numbered time periods between the cathodes alternately and the pairs of pins alternately, the cathodes being negative during said odd numbered cycles, said voltage being applied during even numbered time periods between the pairs of pins alternately, the polarity being reversed between said pairs of pins during alternate even numbered time periods.

9. A method of treating a bone fracture comprising the steps of:
   (a) fixing the site of the bone fracture including the steps of inserting a first pair of fixation pins one on each side of said site, and inserting a second pair of fixation pins one on each side of said site;
   (b) orienting a cathode with the distal end thereof in electrical contact with the bone adjacent the fracture site therein; and
   (c) applying a voltage cyclically during odd numbered and even numbered time periods, applying said voltage during odd numbered time periods between said cathode and the pairs of pins alternately, the cathode being negative during said odd numbered cycles, applying said voltage during even numbered time periods between the pairs of pins alternately, the polarity being reversed between said pairs of pins during alternate even numbered periods.

10. The method of claim 9 further comprising the step of adjusting the lateral position of the cathode with respect to the fractured bone.

11. The method of claim 9 further comprising the step of adjusting the axial position of the cathode about the fractured bone.

12. A method of treating a bone fracture comprising the steps of:
   (a) fixing the site of the bone fracture including the steps of inserting a first pair of fixation pins one on each side of said site, and inserting a second pair of fixation pins one each side of said site;
   (b) orienting at least one cathode with the distal end thereof in electrical contact with the bone adjacent the fracture site therein; and
   (c) applying a voltage cyclically during odd numbered and even numbered time periods, applying said voltage during odd numbered time periods between at least one cathode alternately and the pairs of pins alternately, at least one cathode being negative during said odd numbered cycles, applying said voltage during even numbered time periods between the pairs of pins alternately, the polarity being reversed between said pairs of pins during alternate even numbered time periods.

13. A method of treating a bone fracture comprising the steps of:
   (a) fixing the site of the bone fracture with a fixation device, including inserting a first pair of fixation pins one on each side of said site, and inserting a second pair of fixation pins one on each side of said site;
   (b) fixing a plurality of cathodes to said external fixation device;
   (c) adjusting the position of said cathodes with the distal end thereof in electrical contact with the bone adjacent the fracture site therein; and
   (d) applying a voltage cyclically during odd numbered and even numbered time periods, applying said voltage during odd numbered time periods between the cathodes alternately and the pairs of pins alternately, the cathode being negative during said odd numbered cycles, applying said voltage during even numbered time periods between the pairs of pins alternately, the polarity being reversed between said pairs of pins during alternate even numbered time periods.

14. A method of treating a bone fracture comprising the steps of:
   (a) fixing the site of the bone fracture with an external fixation device, including inserting a first pair of fixation pins one on each side of said site, and inserting a second pair of fixation pins one on each side of said site;
   (b) fixing first, second, third and fourth cathodes to an adjustable member forming a portion of said external fixation device;
   (c) adjusting the position of said member to orient said cathodes with the distal end thereof in electrical contact with the bone adjacent the fracture site therein; and
   (d) applying a voltage cyclically during odd numbered and even numbered time periods, the cathodes at all times having either no voltage or negative voltage applied thereto, the pins having either positive, negative or no voltage applied thereto, either the first pair of pins or the second pair of pins being positive when a negative voltage is applied to any cathode, the voltage application being cycled to cause electron flow from the first cathode to the first pair of pins in a first period, from the first pair of pins to the second pair of pins during a second period, from the second cathode to the second pair of pins in third period, from the second pair of pins to the first pair of pins in fourth period, from the third cathode to the first pair of pins in the fifth period, from the first pair of pins to the second pair of pins in the sixth period, from the fourth cathode to the second pins in the seventh period, and from the second pair of pins to the first pair of pins in the eighth period.

* * * * *